United States Patent [19]

Hunt et al.

[11] Patent Number: 4,512,349

[45] Date of Patent: Apr. 23, 1985

[54] METHOD OF DIRECT TISSUE GAS TENSION MEASUREMENT AND APPARATUS THEREFOR

[75] Inventors: Thomas K. Hunt; William H. Goodson, III; Ning Chang; David R. Knighton, all of San Francisco, Calif.; Finn Gottrup, Hojbjerg, Denmark; Richard Firmin, London, England

[73] Assignee: Regents of the University of California, Berkeley, Calif.

[21] Appl. No.: 494,173

[22] Filed: May 13, 1983

[51] Int. Cl.³ .............................................. A61B 5/00
[52] U.S. Cl. ..................................... 128/632; 128/635
[58] Field of Search ............... 128/630, 632, 635, 748; 55/158, 270

[56] References Cited

U.S. PATENT DOCUMENTS

| | | | |
|---|---|---|---|
| 3,893,448 | 7/1975 | Brantigan | 128/632 |
| 3,983,864 | 10/1976 | Sielaff et al. | 128/632 |
| 4,005,700 | 2/1977 | Parker | 128/632 |
| 4,016,863 | 4/1977 | Brantigan | 128/632 |
| 4,016,864 | 4/1977 | Sielaff et al. | 128/632 |
| 4,041,933 | 8/1977 | Reichenberger | 128/635 |
| 4,158,305 | 4/1979 | Reichenberger | 128/635 |
| 4,244,713 | 1/1981 | Goodwin | 128/632 X |
| 4,340,615 | 7/1982 | Goodwin et al. | 128/635 X |

Primary Examiner—Edward M. Coven
Attorney, Agent, or Firm—Flehr, Hohbach, Test, Albritton & Herbert

[57] ABSTRACT

A new method of tissue oxygen tension measurement which is suitable for human use utilizes an implanted Silastic tube which is inserted through four to five cm of subcutaneous tissue leaving the ends exposed. With the tube filled, for example, with a saline solution, reference and oxygen electrodes are inserted at the exposed ends and by the use of a polarographic potential the amount of oxygen which permeates through the tube from the tissue into the saline solution may be measured on a continuous real-time basis.

27 Claims, 9 Drawing Figures

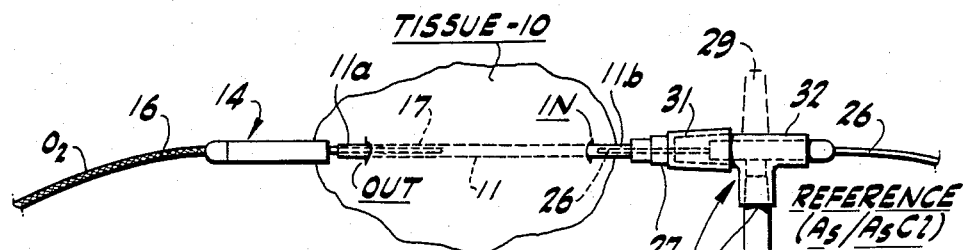
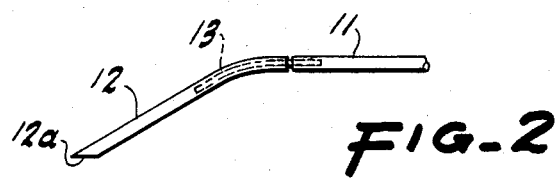
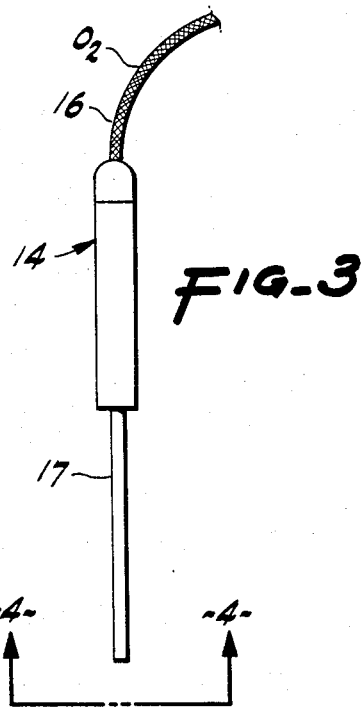
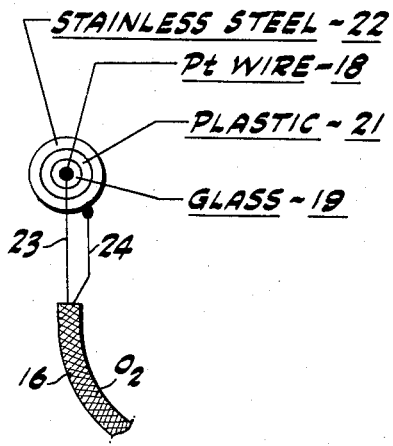

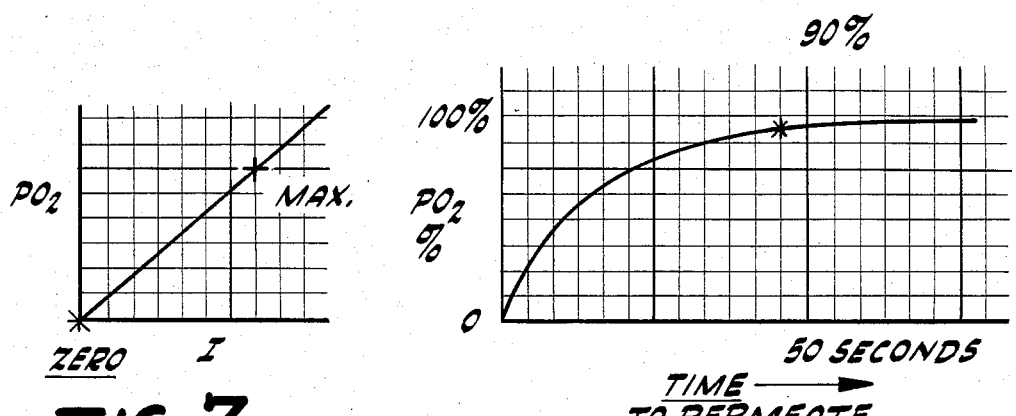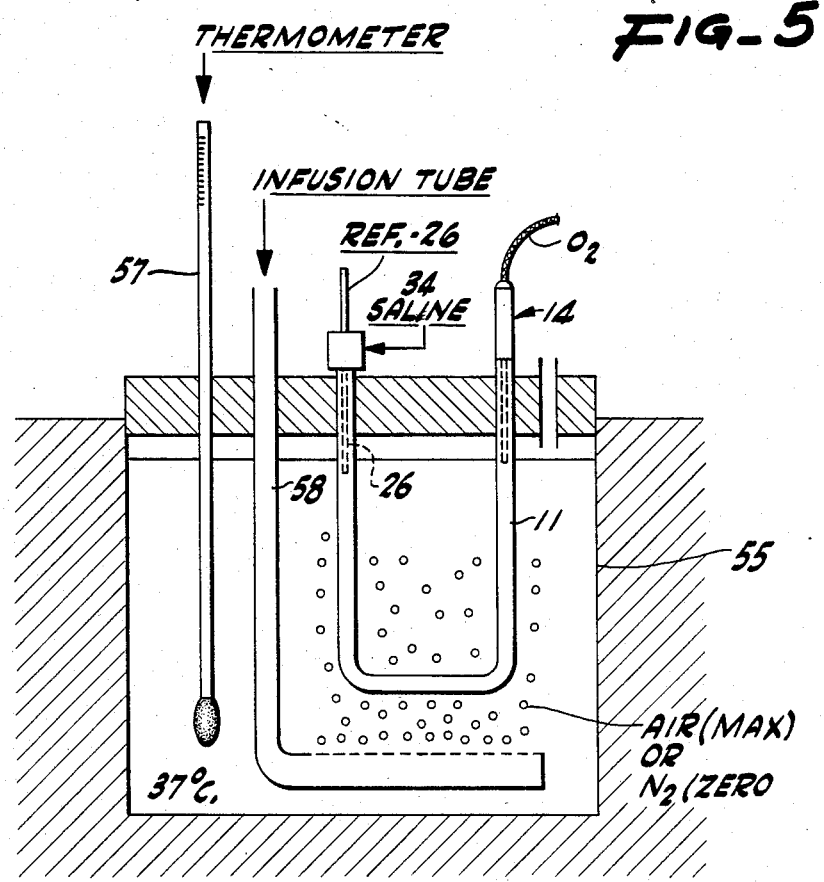

METHOD OF DIRECT TISSUE GAS TENSION MEASUREMENT AND APPARATUS THEREFOR

This invention was made with Government support under Grant No. GM 27345 awarded by the Department of Health and Human Services. The Government has certain rights in this invention.

The present invention is directed to a method of direct tissue gas tension measurement and apparatus therefor and more specifically to a method utilizing a gas permeable tube implanted in the tissue and where gas polarography is used for the real-time measurement of the amount of oxygen in the human tissue.

There have been and are several currently available methods to measure tissue oxygen in a human patient. A Brantigan U.S. Pat. No. 4,016,863, issued Apr. 12, 1977, discloses a tissue gas diffusion catheter device which is inserted into the tissue and the fluid therein is allowed to become equilibrated with the gas contained in the surrounding body tissue. Specifically, oxygen contained in this surrounding body tissue diffuses through the Teflon wall of the catheter into the contained fluid. Thereafter, the equilibrated or "tonometered" fluid is analyzed by, for example, a mass spectrometer or a blood gas analyzing instrument which is available in hospital laboratories. Such blood gas instrument may utilize an oxygen polarographic technique to analyze the fluid which has been placed in the table mounted instrument.

A variation of this method has been used in patients where a Silastic tube is implanted which allows tissue oxygen to equilibrate across the Silastic with the fluid that has been introduced into the Silastic tube. This fluid is then removed and analyzed at a remote fluid-gas analyzer as discussed above. Such technique was found to require prohibitive amounts of skill and labor and thus unsuited to routine clinical use.

In the foregoing Silastic implanted tissue tonometer, as described in the Brantigan patent, in one mode of use a water solution is pumped through the tubing at a sufficiently slow rate to allow the water to become equilibrated with tissue gases. The exiting fluid is then conducted in a continuous flow to the inlet of a standard clinical blood gas instrument at the bedside, and the gas content analyzed. One difficulty here is the "use of the expensive blood gas analyzing instrument" which must be at the patient's bedside; in addition, the great time lag and resulting inaccuracies produced by the slow moving fluid. Another difficulty is occasioned by the need for hydraulic connections, stiff tubes and pumps which restrict allowable patient motion.

Another type of instrument utilizes ultra-thin platinum electrodes to develop microelectrode oxygen potentials. These microelectrodes are extremely precise. However, since they are directly inserted into the tissue, they may be contaminated by tissue proteins which may alter their calibration. Also their position in tissue relative to blood vessels profoundly affects the measured value. Therefore, a number of readings must be taken from different sites and a mean value calculated. Microelectrode systems are also difficult to handle and fragile and therefore unsuited to routine clinical use.

One type of "bare" platinum electrode which is inserted into tissue is, for example, produced by the Diamond Electro-Tech, Inc. of Ann Arbor, Mich. (formerly Transidyne General Corporation) under a type 760 oxygen electrode. Here there is a platinum wire encased in a glass, plastic, stainless steel sheath. The electrode system is always poisoned by tissue proteins, and this method is not acceptable for clinical use.

Measurement of oxygen percutaneously with a heated skin device has been utilized successfully. While this is a non-invasive device which is placed on the skin, its success requires that the skin be heated to erythema to obtain measurable oxygen concentrations. This causes a major change in local perfusion. Furthermore, heating causes changes in skin lipid structure and shifts the oxygen-hemoglobin disassociation curves of the blood in that of the skin to the right. Serious burns due to its use have been reported.

It is, therefore, an object of the present invention to provide a method and apparatus therefor of direct tissue gas tension measurement which has a real-time read-out and which is simply inexpensive and accurate and lends itself to clinical use as opposed to laboratory use.

In accordance with the above object, there is provided a method of direct tissue gas tension measurement by use of a gas permeable tube implanted in such tissue and by gas polarography comprising the steps of implanting a predetermined length of the tube through the tissue and leaving a pair of exposed ends. Thereafter, reference and gas electrodes are inserted in the respective ends of the tube and it is filled with an electrolytic fluid. Oxygen permeates from the tissue through the tube into the liquid. A polarographic potential is applied between the gas and reference electrodes and the electrical signal from the gas electrode is measured. An equivalent apparatus is provided.

FIG. 1 is a top view of the apparatus of the invention as used on a human patient with enlarged portions.

FIG. 2 is a side view of a portion of the apparatus used in implementing the method of the invention.

FIG. 3 is an elevation view of one of the electrodes of the present invention.

FIG. 4 is a greatly enlarged end view taken along line 4—4 of FIG. 3 also showing its connection to the electrical circuitry.

FIG. 5 is a characteristic curve useful in understanding the invention.

FIG. 7 is a graph useful in understanding the invention.

FIG. 8 is a cross-sectional view of calibration apparatus used in conjunction with the present invention.

Figure 6:
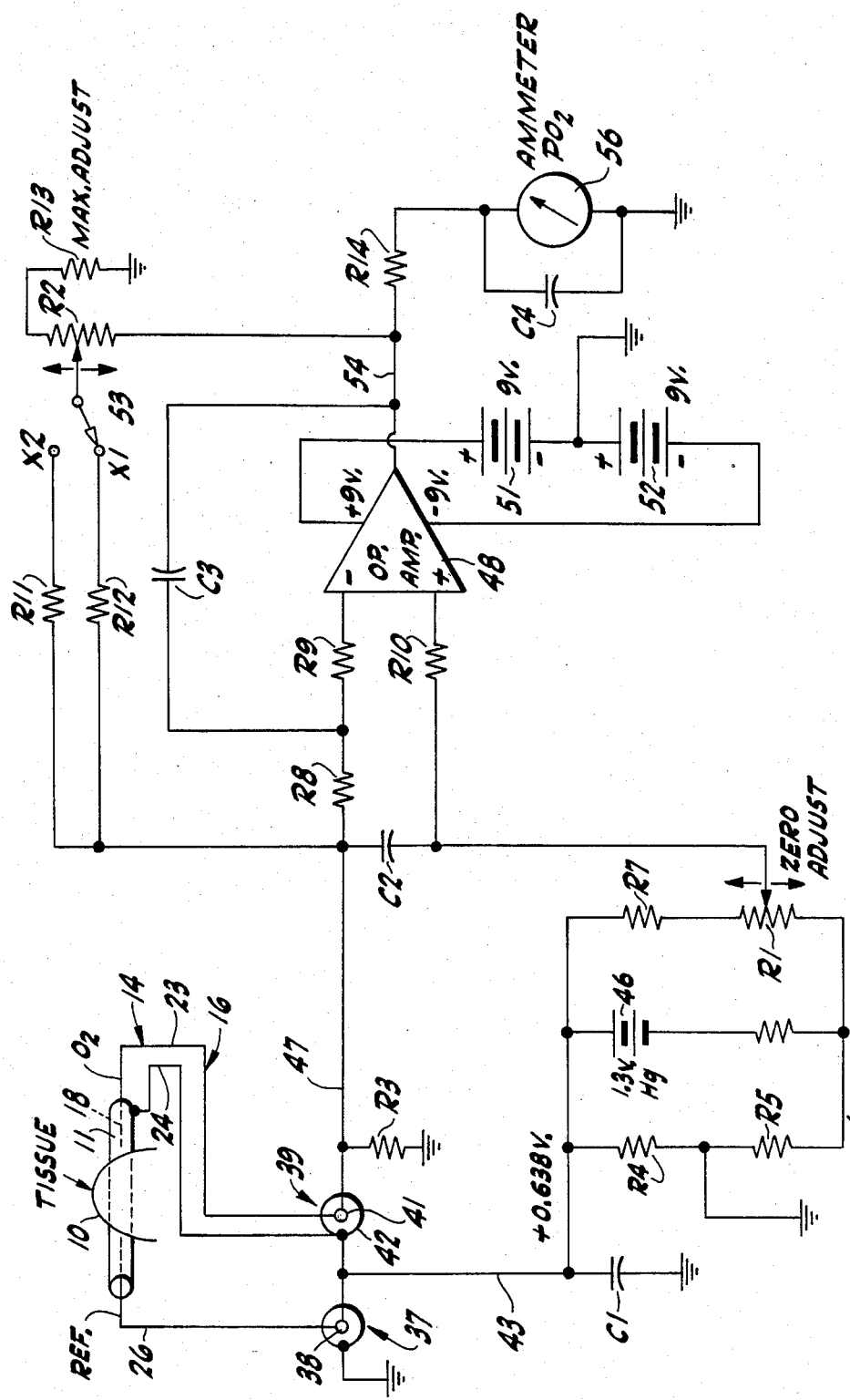
FIG. 6 is a circuit schematic embodying the present invention.

FIG. 1 shows the apparatus of the present invention as it would be used on a human patient. In the subcutaneous tissue 10, is implanted an approximately four centimeter length of Silastic tubing 11 which is permeable to the oxygen or other gas contained in the tissue. It is impermeable to fluids in the tissue and especially fluids containing protein which might otherwise contaminate the measuring electrodes. In the drawing, the tube is shown at 11a as exiting or coming "out" of the skin; 11b labeled "in" is the insertion point of the tube. Thus, the tube ends 11a and 11b of the gas permeable tube are exposed and may have electrodes inserted as shown.

• Referring briefly to FIG. 2, this illustrates a spinal needle 12 which has fitted within it a mandrel 13 on which is fitted and glued one end of tube 11. Thus, as is apparent, the outer diameter of the tube is matched to the outer diameter of the spinal needle so that insertion of the sharpened end 12a of this spinal needle through the tissue creates a hole in the tissue of the same diameter as the tube. This prevents the unwanted formation of, for example, tissue serum which may affect the accuracy of measurement; or rather the transfer of a representative sample of the tissue oxygen into the electrolytic fluid contained within the tube 11.

The spinal needle as illustrated in FIG. 2 is bent to maintain the mandrel within the needle and to facilitate placement of the needle through skin.

For implantation, needle 12 is inserted by the medical personnel subcutaneously by passing it through the skin into the subcutaneous layer, keeping it parallel to the skin for four cm, and passing it out through the skin again. The Silastic tubing 11 follows in the needle track as illustrated in FIG. 1. The needle and excess tubing are then cut off and the tube is secured in place with sutures or sterile tape at its entrance and exit from the skin. Thus, tube ends 11a and 11b are left exposed.

Next, in order to accomplish the polarographic measurement of oxygen from the tissue 10, which will now permeate through the tube into a fluid electrolyte, which will be placed in tube 10, reference and oxygen electrodes are placed in the two exposed ends of the tube. Specifically, at end 11a an oxygen sensitive electrode 14 is placed having a coaxial wire electrode end 17 shown in dashed outline in FIG. 1 which extends approximately one and one-half cm from the point where the tube leaves the skin.

FIG. 3 illustrates the oxygen electrode in greater detail. The cross-section of its end, which is cut off at a 90° angle, is illustrated in FIG. 4. It includes a platinum wire 18 surrounded by a glass sheath 19 and then a plastic sheath 21 and finally a stainless steel outer sheath 22. This is in effect a 21 gauge hypodermic needle with the tip of the platinum wire 18 being approximately 25 microns.

The 90° cutoff as opposed to a beveled tip minimizes the possibility of puncture of the tube during insertion.

The electrical connection to the electrode is also illustrated in FIG. 4 with the center conductor 23 of the coaxial cable 16 being connected to the platinum wire and the outer sheath 24 being connected to the stainless steel sheath 22.

The sheathed bare-tipped oxygen electrode 14 is available as model 760 from Transidyne General Corporation of Ann Arbor, Mich. which as discussed above is now Electro-Tech, Inc. And, as also discussed, it is not suitable for clinical use by direct insertion in the tissue because the platinum is always poisoned by tissue protein deposited on it.

Now again, referring to FIG. 1, the other exposed end 11b of tube 11 has a reference electrode 26 inserted into it. This is accomplished by use of a nylon female hub 27 which is glued onto tube 11 into which is inserted the tapered port of a three-way stopcock valve 28. Such stopcock 28 is manufactured by Pharmaceal, Inc. of Toa Alta, Puerto Rico under model number K75. It is illustrated more fully in U.S. Pat. No. 3,185,179. It is a three-way stopcock which has a handle 29 which in normal use provides for three different flow paths between its three ports 31, 32 and 33. However, the present invention utilizes this stopcock by putting the handle 29 in its fourth position which thereby connects all three ports together as indicated by the dashed lines. Thus, port 31 is press fitted into the nylon bushing 27; in port 32, is placed the reference electrode 26 which passes through the stopcock, the nylon hub 27 and into the tube 11. Then onto port 28 is placed a hypodermic syringe 34 containing an electrolytic solution such as sodium or potassium chloride which is then injected into the tube 11, both to flush it and then fill it, so that gas or oxygen from tissue 10 may permeate through the Silastic wall of tube 11 into the saline solution. A gel might also be used.

Reference electrode 26 is of the silver/silver chloride type which is well-known for use in a polarographic technique.

After the tube 11 has been implanted, the electrodes are in place, and the electrolytic fluid has been placed in tube 11, the gas or oxygen in the tissue is allowed to permeate through the tube into the liquid. FIG. 5 illustrates that with the present invention the time to permeate up to, for example, a 90 percent partial pressure value may be as little as 50 seconds. In practice, for clinical accuracy, two or more minutes would be allowed. The curve shows that the permeation of oxygen through the Silastic tubing occurs in an asymptotic mode.

In order to measure the amount of oxygen in the saline liquid in tube 11, and therefore in the tissue 10, a polarization voltage or polarographic potential must be applied between the oxygen and reference electrodes in accordance with well-known polarographic technique. In the case of oxygen, this voltage is approximately 0.64 volts with the oxygen electrode 14 being at a negative potential or the cathode potential. This potential varies from 0.60 to about 0.74 volts depending on the platinum electrode. The signal current from the oxygen electrode is then read by a suitable measuring instrument and its magnitude is proportional to the partial pressure of oxygen in the tissue 10 which is designated $PO_2$.

FIG. 6 illustrates the circuit for applying the polarographic potential of 0.64 volts between the reference and oxygen electrodes 14 and 26. Tube 11 is, of course, shown implanted in tissue 10 with the saline solution within the tube and the polarographic potential of 0.64 volts applied across it. The reference electrode 26 is connected to the coaxial connector 37 and the oxygen electrode 14 to the coaxial connector 39.

With respect to the reference electrode, the central terminal 38 of connector 37 is utilized and this in turn is connected to a source of polarographic potential 44 via line 43. Line 43 is also connected to the outer shield sleeve 42 of coaxial connector 39.

Coaxial cable 16 of oxygen electrode 14 is plugged into connector 39. Thus, the center platinum electrode 18 via line 23 is connected to the center electrode 41 which is connected to common through a resistor R3. Thus, between this common and reference electrode 26, there is the polarographic potential of approximately 0.64 volts. The connection 24 of this potential to the oxygen cable 16 is merely for shielding. Since it is connected as illustrated in FIG. 4 to the stainless steel sheath 22, there is no polarographic action that takes place and this connection, from that standpoint, is irrelevant to the process.

The source of very accurate polarization potential is provided by the electrical circuit 44 which has as its most important part a 1.3 volt highly accurate mercury battery 46. This is in series with a resistor R6.

The final potential is provided by the dividing action of series connected resistors R4 and R5 which are in parallel with battery 46 and resistor R6. The common point of the resistors is also connected to common. A capacitor C1 acts as a radio frequency bypass from the line 43.

The polarographic signal on a line 47 from terminal 41 is connected to the inverting terminal of an operational amplifier 48 through the series resistors R8 and R9. The non-inverting input, via a resistor R10, is connected to a zero adjust potentiometer R1 to provide for adjustment of or regulation of the zero level of the final signal measurement apparatus which, as will be discussed later, is an ammeter 56. Zero adjust potentiometer R1 is in series with R7 and is supplied a very accurate zero adjustment voltage from the same battery 46 as is used to provide the polarographic potential.

Another bypass capacitor C2 connects the inverting and non-inverting terminals of operational amplifier 48. Power is supplied the operational amplifier by batteries 51 and 52, which are both nine volts, to provide respective positive and negative polarities as indicated. Capacitor C3 provides for 60 cycle rolloff, and is connected between the output and back to the inverting input of the amplifier 48. The gain of the amplifier is controlled by feedback resistors R11 and R12 which in conjunction with switch 53, which is connected to a potentiometer R2 and then to the output line 54, provides for a variation of ranges of the amplifier. In practice, this range with respect to ammeter 56 is equivalent to zero to 150 mm of mercury (the partial pressure of the oxygen being measured) or zero to 300 mm of mercury. Output 54 of operational amplifier 48 is connected to ammeter 56 through resistor R4. The ammeter is also bypassed for high frequencies by a capacitor C4. The following values of the various resistor and capacitors have been used. The capacitor values are in microfarads:

| R1 | 10 K  | R8  | 10 M  | C1 | 0.33   |
|----|-------|-----|-------|----|--------|
| R2 | 100 K | R9  | 1 M   | C2 | 0.01   |
| R3 | 22 M  | R10 | 1 M   | C3 | 0.0047 |
| R4 | 7.5 K | R11 | 100 M | C4 | 10     |
| R5 | 8.2 K | R12 | 50 M  |    |        |
| R6 | 100   | R13 | 2.2 K |    |        |
| R7 | 10 K  | R14 | 4 K   |    |        |

The operational amplifier 48 is the type AD (Analog Device) 515.

Because of the very sensitive nature of the oxygen probe 14 and the measurement being conducted, in most cases a calibration must be conducted before the actual measurement on the patient. Sometimes it may be wise to verify results by again calibrating after use. And, at times, it has been found in practice that the system can be used for several days on a patient without need for recalibration.

In any case, with the oxygen electrode of the present invention and the use of the specific polarizing potential for oxygen, it has been found that there is a linear relationship between the output current I read by ammeter 56 and the $PO_2$ (the partial pressure of the oxygen in the saline in tube 11 and thus the tissue). This linear relationship is illustrated in FIG. 7. Thus, only two calibration points, zero and max, are necessary.

For use in calibration, FIG. 8 shows a water bath 55 in which is inserted the actual Silastic tube 11 which is to be implanted in the patient or an equivalent tube. This is not critical. And, as also illustrated in FIG. 1, inserted in one end is the reference electrode 26 along with the saline solution hypodermic 34 and in the other the oxygen electrode 14. A thermometer 57 indicates when the body temperature of 37° C. is reached. For the zero level measurement, nitrogen is passed through the infusion tube 58, time is allowed for the nitrogen to permeate through the Silastic tube 11 into the saline in tube 11, and referring briefly to FIG. 6, the ammeter 56 is set to zero by use of zero adjust potentiometer R1. Alternatively, rather than use nitrogen, the reference electrode may be merely disconnected. However, although some dark current may result from this, in most cases it may be a second order error and thus of no consequence.

For the maximum level, air into the infusion tube 58 is allowed to permeate through the tube 11 and then the maximum level signal is read by ammeter 56. And this adjusted by potentiometer R2 to, if desired, 150 mm of mercury qr 300 mm of mercury.

Figure 9:
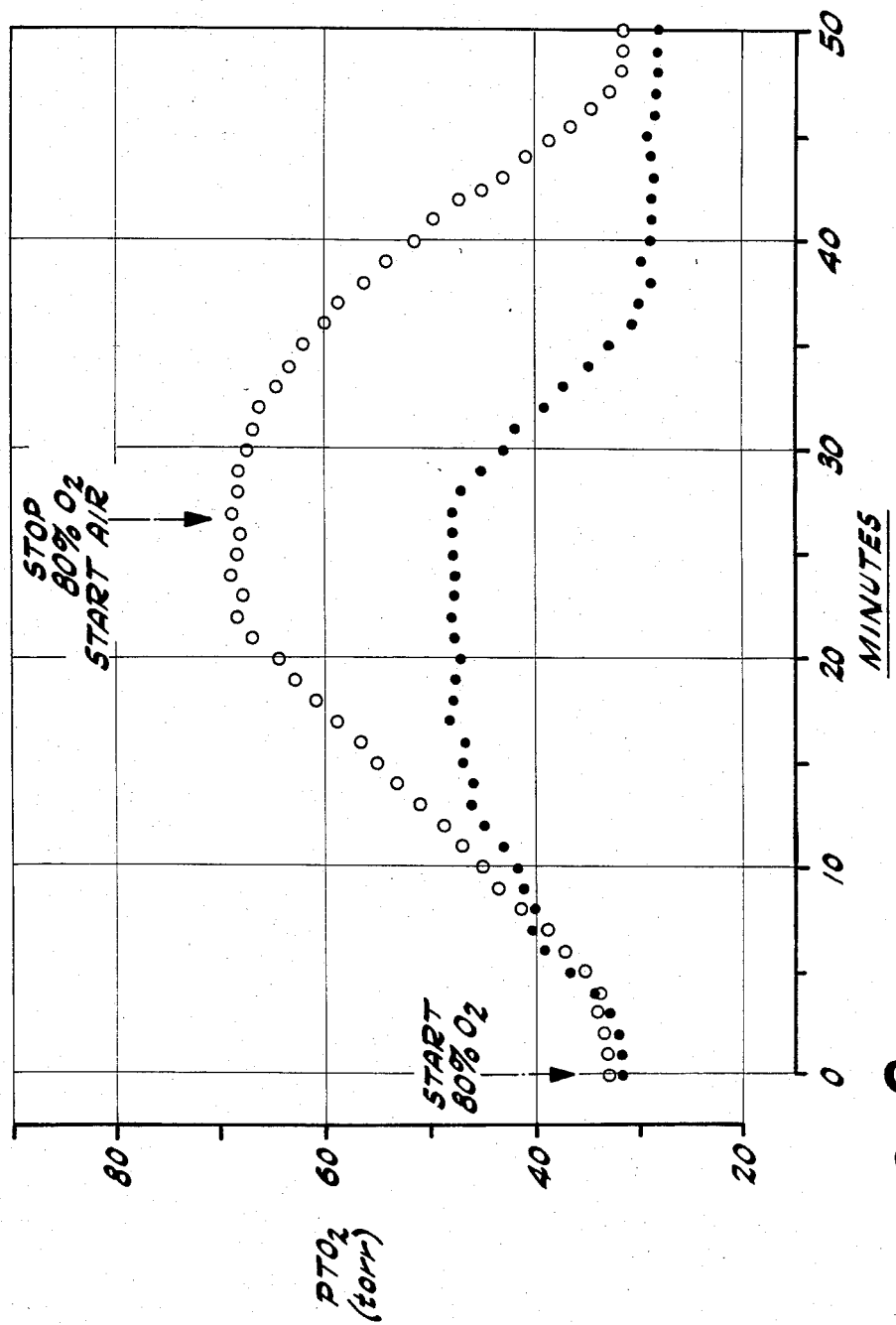
FIG. 9 is a set of curves showing the invention in actual use on a human patient.

The apparatus and method of the present invention has actually been used on several human patients. An example of such use is shown in FIG. 9. Here tissue $PO_2$ was first measured in an immediate post-operative period (that is, after the patient had surgery) where the patient was breathing air. When stability was reached, the subject started to breathe 80 percent oxygen indicated at zero minutes. A continuous recording was made. A typical response to oxygen on the operative day is shown by the top curve with circles. Three post-operative days later is indicated by the lower curve with dots. It indicates on the operative day that there is much greater response to oxygen than at a later time. The FIG. 9 also illustrates that with the present invention that a real-time reading of the actual tissue oxygen partial pressure is provided, thus indicating the actual state of the patient. Referring again to FIG. 5, it has been found that there are many patients with roughly a 50 second response time to a 90 percent level to a step change in $PO_2$; and in general, it has been found that a 95 percent response occurs within 60 to 120 seconds.

One significant and primary advantage of the present invention is that the measurement of tissue oxygen tension, especially on a real-time basis, is a particularly good index of tissue perfusion since it reflects more than just blood supply. Rather, it measures the adequacy of blood supply to meet tissue oxygen needs. As discussed above, there are a variety of techniques available for tissue oxygen measurement. None so far have been suited to routine clinical use. The present invention has devised a new method of subcutaneous oxygen tension measurement which is sufficiently robust (that is, hardy, fast and in real-time), simple, inexpensive and accurate to justify clinical use. The subcutaneous tissue is ideal as a site for measurement since it is readily accessible and contains a vascular bed which is physiologically the first sacrificed when circulatory homeostasis is threatened and the last to be reopened when it is restored.

One of the other advantages of the method of the present invention is the fact that for each day after implantation, for example, in a human patient, there is a definable normal and a definable response to the addition of a specified amount of oxygen to the lungs and hence arterial blood.

First, with respect to the definable normal, it is believed that the insertion of the tubing does cause some damage to the tissue. It has been found that within the first 24 hours of insertion of such tube the response to oxygen may be in the range of from 55–65 ($PTO_2$), and then on the second day 48–55; on the third day 40–48; on the fourth day 35–45; and thereafter, for the fifth and subsequent days, it is in the same 35–45 range. This is partially illustrated, of course, in FIG. 9 which shows the first day with a curve in circles and three days later with a curve in dots. Thus, in actual use, the readings of the first day would have the largest correction factor applied to them for normalization and thereafter the correction factor would be progressively reduced until the fourth day.

Since these readings are somewhat relative, the important factor is that they are reproducible and definable. This is important from a clinical standpoint in that from one patient to the next a reading on a certain day can thus be normalized so that the data can be applied equally to several different patients.

Another factor as illustrated in FIG. 9 is that on successive days as illustrated between the top and bottom curve the transient response upon application of oxygen becomes more rapid as time goes on. For example, in the top curve, there is a time lapse of approximately 20 minutes until a steady state level is reached and in the bottom curve it is approximately 12 to 15 minutes. This definable transient response is also useful for clinical purposes since it indicates when a measurement has reached a steady state condition.

Post-operative monitoring has already been described. Another typical use might be measuring the tension of the anesthetic gases during surgery. Many other uses suggest themselves.

The present method has several advantages over other techniques for measuring tissue oxygen. It provides a single integrated mean or average of the extracellular fluid oxygen tension. In other words, the Silastic tubing in the patient's tissue integrates all the various oxygen tensions impinging on its outer surface to provide an average or integrated mean of the amount of oxygen in that tissue. This is opposed to inserting a single ultra-fine platinum microelectrode in the tissue which gives a very localized value. Furthermore, the platinum electrode, which is necessarily used in this polarographic technique, is protected from protein "poisoning". Thus, there is no worry about the build-up of membrane on the electrode or the shift of values after a short period of use. Thus, the data is amenable to statistical analysis and is highly proportional to regional blood supply and microvascular perfusion.

From the ease of clinical use standpoint, the new method has several advantages. The catheter or Silastic tube is shorter and less traumatic to insert. And the tissue oxygen tension can be measured rapidly and continuously for long periods. There is little flushing of saline through the tubing and artifacts consequent on the amount of partial pressure of oxygen in the saline itself are avoided. The Silastic material has been found to cause minimal discomfort and little tissue reaction. This allows the tube to be removed easily and painlessly after periods as long as two weeks or more. Thus, the present invention readily lends itself to clinical use.

What is claimed is:

1. A method of direct tissue gas tension measurement by use of a gas permeable tube implanted in such tissue and by gas polarography comprising the following steps:
   implanting a predetermined length of said tube through said tissue and leaving a pair of exposed ends of such tube;
   inserting reference and gas electrodes in respective ends of said tube;
   filling said tube with an electrolytic fluid;
   waiting for said gas to permeate from said tissue through said tube into said fluid;
   and applying a polarographic potential between said gas and reference electrodes and measuring the electrical signal from said gas electrode.

2. A method as in claim 1 including the step of calibrating said gas electrode.

3. A method as in claim 2 in which said calibration step is conducted before said tube is implanted.

4. A method as in claim 2 where said calibration step includes placing said tube or an equivalent tube in a water bath, maintaining the water bath at tissue temperature, inserting reference and gas electrodes in the tube ends, applying a polarographic potential across said electrodes, filling said tube with said electrolytic fluid, applying a polarographic potential between said gas and reference electrodes, bubbling in said water bath air allowing it to permeate into said electrolytic fluid within said tube; measuring the resultant electrical signal from the gas electrode, and utilizing this signal as a maximum level, bubbling nitrogen in said water bath allowing it to permeate into the electrolytic fluid within said tube, measuring the resultant electrical signal from the gas electrode, and utilizing this signal as a zero level.

5. A method as in claim 4 where said electrical signal is measured by an ammeter circuit including the step of regulating said ammeter by utilizing said zero and maximum levels of said calibration step.

6. A method as in claim 1 where said implanting step includes the steps of utilizing a spinal needle with a mandrel which fits within the spinal needle, allowing a portion of the mandrel to extend from the end of the needle opposite that of the sharpened end, and fitting on the extended mandrel and gluing thereon such tube whereby the outer diameter of the tube is matched to the outer diameter of the spinal needle so that insertion of the sharpened end of the needle through the tissue creates a hole in the tissue of the same diameter as said tube.

7. A method as in claim 6 in which said mandrel is maintained in said spinal needle by bending such needle.

8. A method as in claim 6 where after said implantation said spinal needle is cut off from said tube to allow insertion of one of said electrodes.

9. A method as in claim 1 in which said polarographic potential is of a magnitude for producing oxygen.

10. A method as in claim 1 where said electrical signal represents the average gas present in the electrolytic fluid throughout the implanted predetermined length of said tube.

11. A method as in claim 1 including the step of measuring said electric signal on successive days and applying a predetermined and different correction factor to such signal for each day.

12. A method as in claim 11 where said correction factor is progressively reduced day-by-day.

13. A method as in claim 12 where said correction factor is a constant after a predetermined number of days.

14. A method as in claim 11 where on successive days the transient response to said gas is different and definable.

15. Apparatus for the direct tension measurement by a gas polarography technique by use of a tube in such tissue comprising:
   a gas permeable tube of relatively small diameter suitable for implantation through said tissue leaving both ends exposed said tube being filled with an electrolytic fluid so that gas from the tissue may permeate through the tube into the fluid;

a gas electrode and a reference electrode inserted into said tube and into said electrolytic fluid at respective ends of the tube;

means for applying a polarographic potential between said gas and said reference electrodes; means for measuring the resultant electrical signal from said gas electrode.

16. Apparatus as in claim 15 including means for calibrating said gas electrode.

17. Apparatus as in claim 15 in which said electrical signal from said gas electrode is measured by an ammeter circuit which is entirely portable and battery powered.

18. Apparatus as in claim 15 in which said polarographic potential is produced by a portable battery source.

19. Apparatus as in claim 18 in which said battery source for the polarographic potential includes a memory cell.

20. Apparatus as in claim 15 in which said tube is of a material substantially impermeable to protein from said tissue to thus protect the gas electrode from protein poisoning.

21. Apparatus as in claim 15 in which said gas electrode is a platinum wire encased in a rigid tubular shield.

22. Apparatus as in claim 15 in which said electrolytic fluid is 0.9 percent saline.

23. Apparatus as in claim 15 in which said reference electrode is a silver/silver chloride electrode.

24. Apparatus as in claim 15 where one end of said tube is coupled to one port of a three port valve, where all ports interconnect, one of said electrodes being inserted through a second port into said electrolytic fluid and the third port being connected to a hypodermic syringe serving as a source of said electrolytic fluid.

25. Apparatus for directly measuring tissue gas tension in tissue subcutaneously comprising:
  (a) A catheter having an oxygen permeable membrane positionable in subcutaneous tissue for directly measuring tissue gas tension;
  (b) an electrolyte in said catheter in chemical contact with the oxygen permeable membrane;
  (c) an electrode sensitive to oxygen in the catheter in electrical contact with said electrolyte; and
  (d) a reference electrode in the catheter in electrical contact with said electrolyte, so that when said catheter is positioned in subcutaneous tissue the oxygen in said tissue permeates said membrane, and reaches chemical equilibrium with the electrolyte and an electrical signal is developed between said oxygen sensitive electrode and said reference electrode corresponding to the tissue gas tension in the subcutaneous tissue.

26. Apparatus as in claim 25 further including means, connectable to said electrodes, for substantially instantaneously indicating the relative tissue gas tension in the subcutaneous tissue.

27. Apparatus as in claim 25 further including means, connectable to said oxygen electrode and said reference electrode, for applying a polarographic potential between said electrodes and for indicating the resultant electrical signal corresponding to the relative tissue gas tension in the subcutaneous tissue.

* * * * *